(12) United States Patent
Dargazanli et al.

(10) Patent No.: US 7,335,670 B2
(45) Date of Patent: Feb. 26, 2008

(54) DERIVATIVES OF N-[HETEROARYL(PIPERIDINE-2-YL) METHYL]BENZAMIDE, PREPARATION METHOD THEREOF AND APPLICATION OF SAME IN THERAPEUTICS

(75) Inventors: Gihad Dargazanli, Cachan (FR); Genevieve Estenne-Bouhtou, Chevilly-Larue (FR); Florence Medaisko, Saint Maur des Fosses (FR); Maria-Carmen Renones, Enghien-les-Bains (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/405,170

(22) Filed: Apr. 17, 2006

(65) Prior Publication Data

US 2006/0223886 A1 Oct. 5, 2006

Related U.S. Application Data

(63) Continuation of application No. PCT/FR2004/002641, filed on Oct. 15, 2004.

(30) Foreign Application Priority Data

Oct. 17, 2003 (FR) ................................. 03 12142

(51) Int. Cl.
  A61K 31/435 (2006.01)
  C07D 405/06 (2006.01)
  C07D 409/06 (2006.01)
  C07D 411/06 (2006.01)
  C07D 413/06 (2006.01)
  C07D 417/06 (2006.01)

(52) U.S. Cl. ............... 514/318; 546/194; 546/209; 546/213; 546/214; 514/326

(58) Field of Classification Search ............... 546/247, 546/246, 193, 209, 194, 213, 214; 514/315, 514/318, 326
See application file for complete search history.

(56) References Cited

U.S. PATENT DOCUMENTS 5,254,569 A * 10/1993 Cheeseman et al. ........ 514/331

FOREIGN PATENT DOCUMENTS

EP   0 499 995   * 8/1992 ............... 401/12
WO   WO 01/81308   11/2001

OTHER PUBLICATIONS

Caulfield et al., J. Med. Chem., 2001, 44, 2679-2682.*

Lopez-Corcuera et al., Molecular Membrane Biology, 2001, 18(1), 13-20.*
Daneman et al., Cell, 2005, 123, 9-12.*
LeBowitz, PNAS, 2005, 102, 14485-14486.*
Banitt et al., J. Med. Chem., 1986, 29, 299-302.*

* cited by examiner

Primary Examiner—Bernard Dentz
Assistant Examiner—David E Gallis
(74) Attorney, Agent, or Firm—Irving Newman

(57) ABSTRACT

Compounds of formula (I) as defined herein:

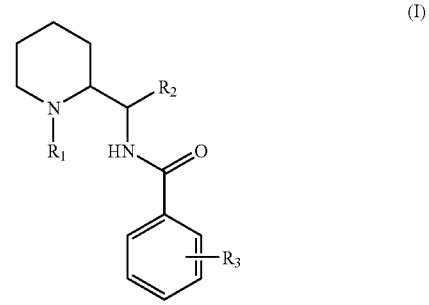

are useful for treating behavioral disorders associated with dementia, psychoses, in particular schizophrenia (deficient form and productive form) and acute or chronic extrapyramidal symptoms induced by neuroleptics; for the treatment of various forms of anxiety, panic attacks, phobias, and compulsive obsessive disorders; for treating various forms of depression, including psychotic depression; for treating disorders caused by alcohol abuse or weaning from alcohol, sexual behavior disorders, eating disorders and for treating migraine. Moreover, the compounds of the invention may be used for treating painful muscle contracture in rheumatology and in acute spinal pathology; for treating spastic contractures of medullary or cerebral origin; for the symptomatic treatment of acute and subacute pain of light to moderate intensity; for treating intense and/or chronic pain, neurogenic pain and intractable pain; for treating Parkinson's disease and Parkinson-like symptoms of neurodegenerative origin or induced by neuroleptics; for treating partial primary and secondary generalized epilepsy of simple or complex symptomology, mixed forms and other epileptic syndromes in addition to another antiepileptic treatment, or in monotherapy, for the treatment of sleep apnea, and for neuroprotection.

5 Claims, No Drawings

DERIVATIVES OF N-[HETEROARYL(PIPERIDINE-2-YL) METHYL]BENZAMIDE, PREPARATION METHOD THEREOF AND APPLICATION OF SAME IN THERAPEUTICS

CROSS-REFERENCE TO RELATED APPLICATIONS

This application is a continuation of PCT/FR2004/002641, filed Oct. 15, 2004, which claims priority from French Patent Application No. 0312142, filed Oct. 17, 2003.

SUMMARY OF THE INVENTION

The compounds of the invention correspond to the general formula (I)

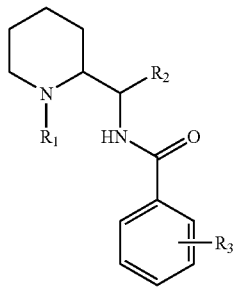

(I)

in which $R_1$ represents either a hydrogen atom, or a linear or branched $(C_1-C_7)$alkyl group optionally substituted with one or more fluorine atoms, or a $(C_3-C_7)$cycloalkyl group, or a $(C_3-C_7)$cycloalkyl$(C_1-C_3)$alkyl group, or a phenyl$(C_1-C_3)$alkyl group optionally substituted with one or two methoxy groups, or a $(C_2-C_4)$alkenyl group, or a $(C_2-C_4)$alkynyl group;

$R_2$ represents a pyridyl, furyl, thienyl, thiazolyl or oxazolyl group, this group being optionally substituted with one or more substituents chosen from halogen atoms and trifluoromethyl and linear or branched $(C_1-C_6)$alkyl and $(C_1-C_6)$alkoxy groups;

$R_3$ represents either a hydrogen atom, or one or more substituents chosen from halogen atoms and trifluoromethyl, linear or branched $(C_1-C_6)$alkyl, $(C_3-C_7)$cycloalkyl, $(C_1-C_6)$alkoxy, phenyl, cyano, acetyl, benzoyl, $(C_1-C_6)$thioalkyl, $(C_1-C_6)$alkylsulfonyl, carboxyl or $(C_1-C_6)$alkoxycarbonyl groups, or a group of general formula $NR_4R_5$ or $SO_2NR_4R_5$ or $CONR_4R_5$ in which $R_4$ and $R_5$ each independently represent a hydrogen atom or a linear or branched $(C_1-C_6)$alkyl or $(C_3-C_7)$cycloalkyl group, or $R_4$ and $R_5$ form, with the nitrogen atom that bears them, a pyrrolidine, piperidine or morpholine ring.

BACKGROUND OF THE INVENTION

Compounds of structure similar to that of the compounds of the invention are described in U.S. Pat. No. 5,254,569 as analgesics, diuretics, anticonvulsivants, anesthetics, sedatives and cerebroprotective agents, via a mechanism of action on the opiate receptors. Other compounds of similar structure are described in patent application EP-0 499 995 as 5-$HT_3$ antagonists that are useful in the treatment of psychotic disorders, neurological diseases, gastric symptoms, nausea and vomiting.

DETAILED DESCRIPTION OF THE INVENTION

The compounds of formula (I) may comprise one or more asymmetric carbon atoms. They may thus exist in the form of threo or erythro enantiomers or diastereoisomers. These enantiomers and diastereoisomers, and also mixtures thereof, including racemic mixtures, form part of the invention.

The compounds of formula (I) may exist in the form of bases or acid-addition salts. Such addition salts form part of the invention.

These salts are advantageously prepared with pharmaceutically acceptable acids, but the salts of other acids that are useful, for example, for the purification or isolation of the compounds of formula (I) also form part of the invention.

The compounds of formula (I) may also exist in the form of hydrates or solvates, i.e. in the form of associations or combinations with one or more water molecules or with a solvent. Such hydrates and solvates also form part of the invention.

The compounds of the invention show particular activity as specific inhibitors of the glycine transporters glyt1 and/or glyt2.

The compounds of general formula (I), of threo or erythro configuration, in which $R_1$ is other than a hydrogen atom may be prepared via a process illustrated by Scheme 1 below.

Scheme 1

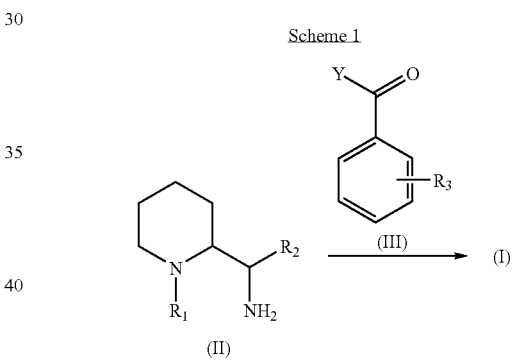

Coupling of a diamine of general formula (II), in which $R_1$ and $R_2$ are as defined above (with $R_1$ other than a hydrogen atom), with an activated acid or an acid chloride of general formula (III) in which Y represents an activated OH group or a chlorine atom and $R_3$ is as defined above, is performed using the methods known to those skilled in the art.

The diamine of general formula (II) may be prepared via a process illustrated by Scheme 2 below.

Scheme 2

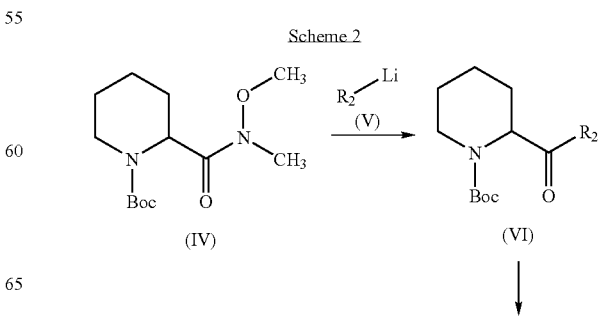

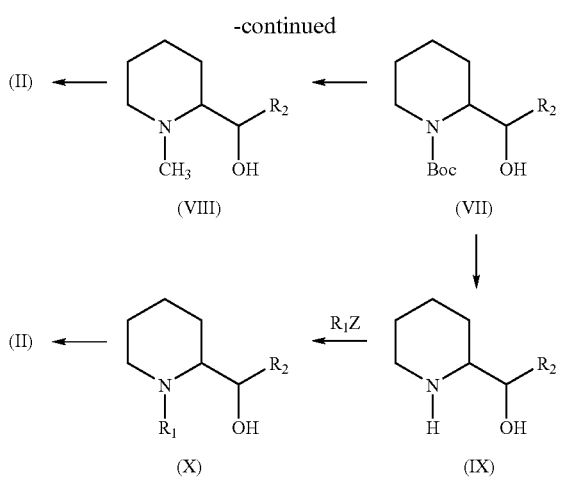

The Weinreb amide of formula (IV), in which Boc denotes a 1,1-dimethylethoxycarbonyl group, is reacted with the lithiated heterocycle of general formula (V), in which $R_2$ is as defined above, in an ether solvent such as diethyl ether, between −90° C. and −30° C.; a ketone of general formula (VI) is obtained, which is reduced to an alcohol of threo configuration of general formula (VII) with a reducing agent such as K-Selectride® or L-Selectride® (potassium or lithium tri-sec-butylborohydride), in an ether solvent such as tetrahydrofuran, between −78° C. and room temperature. The carbamate of general formula (VII) may then be reduced to the threo N-methylamino alcohol of general formula (VIII) via the action of a mixed hydride such as lithium aluminum hydride, in an ether solvent such as tetrahydrofuran, between room temperature and the reflux temperature. The threo alcohol of general formula (VIII) is then converted in two steps into an intermediate diamine of general formula (II) in which $R_1$ represents a methyl group in threo form or an erythro-threo mixture depending on the nature of the heterocycle, in the following manner: the alcohol function is first converted into an electrophilic group, for example a methanesulfonate group, via the action of methanesulfonyl chloride, in a chlorinated solvent such as dichloromethane, and in the presence of a base such as triethylamine, between 0° C. and room temperature, and the electrophilic group is then reacted with liquefied ammonia at −50° C., in an alcohol such as ethanol, in a closed medium such as an autoclave, between −50° C. and room temperature. The carbamate of general formula (VII) may also be deprotected using a strong base such as aqueous potassium hydroxide, in an alcohol such as methanol, to obtain the threo-amino alcohol of general formula (IX), followed by performing an N-alkylation using a halogenated derivative of formula $R_1Z$, in which $R_1$ is as defined above, but other than a hydrogen atom, and Z represents a halogen atom, in the presence of a base such as potassium carbonate, in a polar solvent such as N,N-dimethylformamide, between room temperature and 100° C. The alcohol of general formula (X) thus obtained is then treated as described with respect to the alcohol of general formula (VIII).

The compounds of general formula (I) in which $R_1$ represents a hydrogen atom may be prepared from a compound of general formula (I) in which $R_1$ represents:
either an optionally substituted phenylmethyl group, by deprotecting the nitrogen of the piperidine ring, for example with an oxidizing agent or with a Lewis acid such as boron tribromide, or via hydrogenolysis,
or an alkenyl group, preferably an allyl group, by deprotecting the nitrogen of the piperidine ring, for example with a palladium 0 complex,
to give a compound of general formula (I) in which $R_1$ represents a hydrogen atom.

Moreover, the chiral compounds of general formula (I) corresponding to the (1R,2R)-(1S,2S)-(1S,2R) and (1R,2S) enantiomers of the various erythro/threo diastereoisomers may be obtained by separating the racemic compounds by high-performance liquid chromatography (HPLC) on a chiral column, or via resolution of the racemic amine of general formula (II) by using a chiral acid, such as tartaric acid, camphorsulfonic acid, dibenzoyltartaric acid or N-acetylleucine, by fractional and preferential recrystallization of a diastereoisomeric salt in a solvent of alcohol type, i.e. by enantioselective synthesis according to Scheme 2 using a chiral Weinreb amide of general formula (IV).

The racemic or chiral Weinreb amide of formula (IV) may be prepared according to a method similar to that described in Eur. J. Med. Chem., 35, (2000), 979-988 and J. Med. Chem., 41, (1998), 591-601. The lithiated heterocycles of general formula (V) may be prepared according to methods known to those skilled in the art and similar to those described in J.O.C., 62, (1997), 5484-5496 and Tetrahedron Letters, 35, (1994), 3673-3674.

The halogenated derivatives of formula $R_1Z$ are commercially available.

Certain acids and acid chlorides of general formula (III) are commercially available or, when they are novel, may be obtained according to methods similar to those described in patents EP-0 556 672 and U.S. Pat. No. 3,801,636 and in J. Chem. Soc., (1927), 25, Chem. Pharm. Bull., (1992), 1789-1792, Aust. J. Chem., (1984), 1938-1950 and J.O.C., (1980), 527.

The examples that follow illustrate the preparation of a number of compounds of the invention. The elemental microanalyses, the IR and NMR spectra and the HPLC on a chiral column confirm the structures and enantiomeric purities of the compounds obtained.

The numbers given in parentheses in the titles of the examples correspond to those in the first column of the table given later.

In the compound names, the hyphen "-" forms part of the word, and the underscore mark "_" serves merely to indicate a line break; it should be deleted if a line break does not occur at that point, and should not be replaced either with a normal hyphen or with a space.

EXAMPLE 1 (COMPOUND 2)

2-Chloro-N-[(1-methyl-2-piperidyl)-3-thienylmethyl]-3-trifluoromethylbenzamide hydrochloride 1:1.

1.1. 1,1-Dimethylethyl 2-(3-thienylcarbonyl)piperidine-1-carboxylate.

1.8 g (10.8 mmol) of 3-bromothiophene dissolved in 20 ml of anhydrous diethyl ether are introduced into a 100 ml round-bottomed flask, under an argon atmosphere, and the medium is cooled to −40° C. 4.8 ml (12 mmol) of a 2.5M solution of butyllithium in cyclohexane are then added slowly and the mixture is left at this temperature for 2 hours.

Using a transfer needle, the lithiated heterocycle is added to a solution of 1.5 g (5.5 mmol) of 1,1-dimethylethyl 2-(N-methoxy-N-methylcarbamoyl)piperidine-1-carboxylate in 50 ml of anhydrous diethyl ether cooled to −20° C., and the mixture is allowed to return to room temperature with stirring over 2 hours.

After hydrolysis with saturated aqueous ammonium chloride solution, the aqueous phase is separated out and extracted with ethyl acetate. The combined organic phases are dried over sodium sulfate, filtered and concentrated under reduced pressure, and the residue is purified by column chromatography on silica gel, eluting with a mixture of ethyl acetate and cyclohexane.

1.2 g of a compound in the form of a colorless oil are obtained, which product is used without further purification in the following step.

1.2 1,1-Dimethylethyl threo[hydroxy-(3-thienyl)methyl]piperidine-1-carboxylate 1.2 g (4 mmol) of 1,1-dimethylethyl 2-(3-thienylcarbonyl)piperidine-1-carboxylate are introduced
into 40 ml of anhydrous tetrahydrofuran in a 250 ml round-bottomed flask under an argon atmosphere, the solution is cooled to −78° C., 12 ml (12 mmol) of a 1M solution of L-Selectride® (lithium tri-sec-butylborohydride) in tetrahydrofuran are added dropwise and the mixture is stirred at −78° C. for 5 hours.

The mixture is hydrolyzed slowly under cold conditions with 7 ml of water and 7 ml of aqueous 35% hydrogen peroxide solution, and is allowed to return to room temperature with stirring over 2 hours.

The resulting mixture is diluted with water and ethyl acetate, the phases are separated and the aqueous phase is extracted with ethyl acetate. After washing the combined organic phases, drying over sodium sulfate, filtering and evaporating, the residue is purified by column chromatography on silica gel, eluting with a mixture of ethyl acetate and cyclohexane.

1 g of product is obtained in the form of a colorless oil, which is used without further purification in the following step.

1.3. Threo-(1-methyl-2-piperidyl)(3-thienyl)methanol.

0.63 g (16.6 mmol) of lithium aluminum hydride is introduced into 10 ml of anhydrous tetrahydrofuran in a 50 ml two-necked flask, under a nitrogen atmosphere, the mixture is heated to reflux, 1 g (3.3 mmol) of a solution of 1,1-dimethylethyl threo-[hydroxy(3-thienyl)methyl]-piperidine-1-carboxylate in 35 ml of tetrahydrofuran is added and the mixture is refluxed for 2 hours.

The mixture is cooled, hydrolyzed slowly with 0.1M potassium sodium tartrate solution and stirred overnight.

The resulting mixture is filtered, the precipitate is rinsed with tetrahydrofuran and the filtrate is then concentrated under reduced pressure. 0.6 g of a colorless oily product is obtained.

1.4. (1-Methyl-2-piperidyl)(3-thienyl)methanamine.

0.6 g (2.8 mmol) of threo-(1-methyl-2-piperidyl)(3-thienyl)methanol and 0.4 ml (2.8 mmol) of triethylamine are introduced into 10 ml of anhydrous dichloromethane in a 50 ml round-bottomed flask, under a nitrogen atmosphere, the medium is cooled to 0° C., 0.22 ml (2.8 mmol) of methanesulfonyl chloride is added and the mixture is allowed to return slowly to room temperature over 1 hour and is concentrated under reduced pressure. Liquefied ammonia is introduced into an autoclave equipped with a magnetic stirrer and cooled to −50° C., a solution of the crude methanesulfonate prepared above dissolved in 30 ml of absolute ethanol is added, the autoclave is closed and the mixture is stirred for 48 hours.

The mixture is transferred into a round-bottomed flask and concentrated to dryness, the residue is diluted with water and dichloromethane, the phases are separated and the aqueous phase is extracted with dichloromethane. After washing the combined organic phases, drying over sodium sulfate, filtering and evaporating off the solvents, 0.5 g of amine is isolated in the form of an oily compound, which is used without further purification in the following step.

1.5 2-Chloro-N-[(1-methyl-2-piperidyl)(3-thienyl)methyl]-3-trifluoromethylbenzamide hydrochloride 1:1

0.25 g (1.17 mmol) of (1-methyl-2-piperidyl)(3-thienyl)methanamine and 0.26 ml (1.4 mmol) of triethylamine dissolved in 20 ml of dichloromethane at 0° C. are introduced into a 50 ml round-bottomed flask. A solution of 0.34 g (1.4 mmol) of 2-chloro-3-trifluoromethylbenzoyl chloride in 10 ml of dichloromethane is then added and the mixture is allowed to return to room temperature with stirring over 2 hours.

The mixture is treated with water and extracted several times with dichloromethane. After washing the organic phases with water and then with aqueous 1N sodium hydroxide solution, drying over magnesium sulfate, filtering and evaporating off the solvent under reduced pressure, the residue is purified by column chromatography on silica gel, eluting with a mixture of dichloromethane and methanol. 0.23 g of oily product is obtained, which is isolated in hydrochloride form using a 0.1N solution of hydrogen chloride in 2-propanol.

0.11 g of hydrochloride is finally isolated in the form of a white solid composed of a mixture of threo/erythro diastereoisomers in an 83/17 ratio.

Melting point: 124-126° C.

EXAMPLE 2 (COMPOUND 6)

Threo-2-chloro-3-methyl-N-[(1-allyl-2-piperidyl)-3-pyridylmethyl]benzamide hydrochloride 1:1

2.1. 1,1-Dimethylethyl 2-(3-pyridylcarbonyl)piperidine-1-carboxylate 14.5 g (91.8 mmol) of 3-bromopyridine dissolved in 100 ml of anhydrous diethyl ether are introduced into a 500 ml round-bottomed flask, under an argon atmosphere, and the medium is cooled to −78° C. 40.4 ml (100.9 mmol) of a 2.5M solution of butyllithium in cyclohexane are then added slowly and the mixture is left at this temperature for 0.5 hour.

A solution of 10 g (36.7 mmol) of 1,1-dimethylethyl 2-(N-methoxy-N-methylcarbamoyl)piperidine-1-carboxylate in 50 ml of anhydrous diethyl ether cooled to −78° C. is added and the mixture is left at this temperature for 2 hours with stirring and then for 12 hours at room temperature.

After hydrolysis with saturated aqueous ammonium chloride solution, the aqueous phase is separated out and extracted with ethyl acetate. The combined organic phases are dried over sodium sulfate, filtered and concentrated under reduced pressure, and the residue is purified by column chromatography on silica gel, eluting with a mixture of ethyl acetate and cyclohexane.

5.5 g of a compound in the form of a colorless oil are obtained, which product is used without further purification in the following step.

2.2. 1,1-Dimethylethyl threo-[hydroxy(3-pyridyl)methyl]piperidine-1-carboxylate.

5.4 g (18.6 mmol) of 1,1-dimethylethyl 2-(3-pyridylcarbonyl)piperidine-1-carboxylate are introduced into 220 ml of anhydrous tetrahydrofuran in a 500 ml round-bottomed flask, under an argon atmosphere, the solution is cooled to −78° C., 55.8 ml (55.8 mmol) of a 1M solution of L-Selectride® (lithium tri-sec-butylboro-hydride) in tetrahydrofuran are added dropwise and the mixture is stirred at −78° C. for 3 hours.

The mixture is hydrolyzed slowly under cold conditions with 67 ml of water and 67 ml of aqueous 35% hydrogen peroxide solution, and is allowed to return to room temperature with stirring over 2 hours.

The mixture is diluted with water and ethyl acetate, the phases are separated and the aqueous phase is extracted with ethyl acetate. After washing the combined organic phases, drying over sodium sulfate, filtering and evaporating, the residue is purified by column chromatography on silica gel, eluting with a mixture of ethyl acetate and cyclohexane.

4.13 g of product are obtained in the form of a colorless oil, which is used without further purification in the following step.

2.3. Threo-3-pyridyl(2-piperid-2-yl)methanol.

A solution of 0.5 g (1.71 mmol) of 1,1-dimethylethyl threo-[hydroxy(3-pyridyl)methyl]piperidine-1-carboxylate in 6 ml of ethanol is placed in a 50 ml round-bottomed flask, an aqueous potassium hydroxide solution prepared from 0.5 g of potassium hydroxide pellets and 3 ml of water is added and the mixture is refluxed for 2 hours.

The mixture is cooled, the solvent is evaporated off under reduced pressure, water is added and the mixture is extracted several times with dichloromethane. After washing the combined organic phases, drying over magnesium sulfate, filtering and evaporating off the solvent under reduced pressure, 0.3 g of a white solid is obtained, which is used without further purification in the following step.

2.4. Threo-1-allyl-2-piperidyl(3-pyridyl)methanol.

0.3 g (1.56 mmol) of threo-3-pyridyl(2-piperid-2-yl)methanol and 10 ml of acetonitrile are introduced into a 50 ml round-bottomed flask equipped with a magnetic stirrer and a circulation of argon. 0.32 g of potassium carbonate and 0.17 ml (1.2 eq) of allyl bromide are then added to the suspension obtained. The suspension is stirred for 6 hours at 25° C. 10 ml of water and 10 ml of ethyl acetate are added, the phases are separated by settling, the aqueous phase is extracted three times with 10 ml of ethyl acetate and the combined organic phases are washed with 50 ml of water and then with 500 ml of saturated sodium chloride solution. The resulting solution is dried over sodium sulfate and filtered, and the solvents are removed under reduced pressure. 0.22 g of a yellow oil is obtained, which is purified by column chromatography on silica gel (120 g column and elution gradient of from 2% to 10% methanol in dichloromethane over 30 minutes). 0.10 g is isolated in the form of a yellow oil.

2.5. Threo-(1-allyl-2-piperidyl)(3-pyridyl)methylamine.

0.71 g (3.05 mmol) of threo-1-allyl-2-piperidyl(3-pyridyl)methanol and 0.43 ml (3.05 mmol) of triethylamine are introduced into 15 ml of anhydrous dichloromethane in a 50 ml round-bottomed flask, under a nitrogen atmosphere, the medium is cooled to 0° C., 0.23 ml (3.05 mmol) of methanesulfonyl chloride is added and the mixture is allowed to return slowly to room temperature over one hour and is concentrated under reduced pressure.

Liquefied ammonia is introduced into an autoclave equipped with a magnetic stirrer and cooled to −50° C., a solution of the crude methanesulfonate prepared above dissolved in 30 ml of absolute ethanol is added, the autoclave is closed and the mixture is stirred for 48 hours.

The mixture is transferred into a round-bottomed flask and concentrated to dryness, the residue is diluted with water and with dichloromethane, the phases are separated and the aqueous phase is extracted with dichloromethane. After washing the combined organic phases, drying over sodium sulfate, filtering and evaporating, 0.57 g of amine is isolated in the form of an oily compound, which is used without further purification in the following step.

2.6. Threo-2-chloro-3-methyl-N-[(1-allyl-2-piperidyl)-3-pyridylmethyl]benzamide 1:1.

0.22 g (1.28 mmol) of 2,3-dichlorobenzoic acid, 0.25 g (1.29 mmol) of 1-[3-(dimethylamino)propyl]-3-ethylcarbodiimide hydrochloride and 0.17 g (1.29 mmol) of hydroxybenzotriazole are successively introduced into 10 ml of dichloromethane in a 50 ml round-bottomed flask and the mixture is stirred at room temperature for 1 hour.

0.3 g (1.29 mmol) of threo-(1-allyl-2-piperidyl)(3-pyridyl)methylamine dissolved in 4 ml of dichloromethane is added and stirring is continued for 15 hours. The mixture is treated with water and extracted several times with dichloromethane. After washing the organic phases with water and then with aqueous 1N sodium hydroxide solution, drying over magnesium sulfate, filtering and evaporating off the solvent under reduced pressure, the residue is purified by column chromatography on silica gel, eluting with a mixture of dichloromethane and methanol. 0.15 g of an oily product is obtained, which is isolated in hydrochloride form using a 0.1N solution of hydrogen chloride in 2-propanol.

0.10 g of hydrochloride is finally isolated in the form of a white solid.

Melting point: 149-151° C.

The table that follows illustrates the chemical structures and the physical properties of a number of compounds of the invention.

In the "salt" column, "−" denotes a compound in base form and "HCl" denotes a hydrochloride.

TABLE

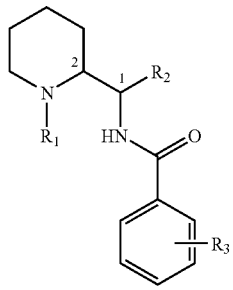

(I)

| No | R₁ | R₂ | R₃ | Salt | m.p. (° C.) | Stereochemistry |
|----|----|----|----|------|-------------|-----------------|
| 1 | CH₃ | 2-methylthiazol-4-yl | 2-Cl, 3-CF₃ | HCl | 131-133 | Threo/Erythro 0/100 |
| 2 | CH₃ | 4-methylthiophen-3-yl | 2-Cl, 3-CF₃ | HCl | 124-126 | Threo/Erythro 83/17 |
| 3 | CH₃ | 4-methylthiophen-3-yl | 2-CH₃, 3-CF₃ | HCl | 139-141 | Threo/Erythro 62/38 |
| 4 | CH₃ | 5-methylthiophen-2-yl | 2-CH₃, 3-CF₃ | HCl | 166-168 | Threo/Erythro 7/93 |
| 5 | CH₃ | 5-methylthiophen-2-yl | 2-Cl, 3-CF₃ | HCl | 168-170 | Threo/Erythro 0/100 |
| 6 | CH₂—CH=CH₂ | 5-methylpyridin-3-yl | 2-Cl, 3-CH₃ | HCl | 149-151 | Threo/Erythro 100/0 |
| 7 | CH₂—CH=CH₂ | 5-methylpyridin-3-yl | 2-Cl, 3-CF₃ | HCl | 144-146 | Threo/Erythro 100/0 |

The compounds of the invention were subjected to a series of pharmacological tests that demonstrated their value as therapeutically active substances.

Study of Glycine Transportation in SK-N-MC Cells Expressing the Native Human Transporter glyt1

The uptake of [$^{14}$C]glycine is studied in SK-N-MC cells (human neuroepithelial cells) expressing the native human transporter glyt1 by measuring the radioactivity incorporated in the presence or absence of the test compound. The cells are cultured as a monolayer for 48 hours in plates pretreated with 0.02% fibronectin. On the day of the experiment, the culture medium is removed and the cells are washed with Krebs-HEPES buffer ([4-(2-hydroxyethyl)-1-piperazineethanesulfonic acid) at pH 7.4. After preincubation for 10 minutes at 37° C. in the presence either of buffer (control batch) or of test compound at various concentrations or of 10 mM glycine (determination of the nonspecific uptake), 10 μM of [$^{14}$C]glycine (specific activity 112 mCi/mmol) are then added. Incubation is continued for 10 minutes at 37° C., and the reaction is quenched by washing twice with pH 7.4 Krebs-HEPES buffer. The radioactivity incorporated by the cells is then estimated after adding 100 μl of liquid scintillant and stirring for 1 hour. Counting is performed on a Microbeta Tri-lux™ counter. The efficacy of the compound is determined by means of the IC$_{50}$, which is the concentration of compound that reduces by 50% the specific uptake of glycine, defined by the difference in radioactivity incorporated by the control batch and the batch that received 10 mM of glycine.

The compounds of the invention that are the most active, in this test, have an IC$_{50}$ of about from 0.001 to 1 μM.

Study of the Glycine Transportation in Mouse Spinal Cord Homogenate

The uptake of [$^{14}$C]glycine by the transporter glyt2 is studied in mouse spinal cord homogenate by measuring the radioactivity incorporated in the presence or absence of test compound.

After euthanizing the animals (male OF1 Iffa Credo mice weighing 20 to 25 g on the day of the experiment), the spinal cord of each animal is rapidly removed, weighed and stored on ice. The samples are homogenized in pH 7.4 Krebs-HEPES buffer ([4-(2-hydroxyethyl)-1-piperazineethanesulfonic acid), in a proportion of 25 ml/g of tissue.

50 µl of homogenate are preincubated for 10 minutes at 25° C. in the presence of pH 7.4 Krebs-HEPES buffer and of test compound at various concentrations, or of 10 mM of glycine to determine the nonspecific uptake. [$^{14}$C]glycine (specific activity=112 mCi/mmol) is then added over 10 minutes at 25° C. to a final concentration of 10 µM. The reaction is quenched by vacuum filtration and the radioactivity is estimated by solid scintillation by counting on a Microbeta Tri-lux™ counter. The efficacy of the compound is determined by means of the IC$_{50}$, the concentration capable of reducing by 50% the specific uptake of glycine, defined by the difference in radioactivity incorporated by the control batch and the batch that received 10 mM of glycine.

The compounds of the invention that are the most active in this test have an IC$_{50}$ of less than 1 µM.

It thus appears that the compounds according to the invention are specific inhibitors of the glycine transporters glyt1 and/or glyt2.

The compounds according to the invention may thus be used for the preparation of medicaments, in particular of medicaments that inhibit the glycine transporters glyt1 and/or glyt2.

Thus, according to another of its aspects, a subject of the invention is medicaments comprising a compound of formula (I), or an addition salt thereof with a pharmaceutically acceptable acid, or alternatively a hydrate or a solvate of the compound of formula (I).

The compounds of the invention may be used especially for treating behavioral disorders associated with dementia, psychoses, in particular schizophrenia (deficient form and productive form) and acute or chronic extrapyramidal symptoms induced by neuroleptics, for the treatment of various forms of anxiety, panic attacks, phobias, compulsive obsessive disorders, for treating various forms of depression, including psychotic depression, for treating disorders caused by alcohol abuse or weaning from alcohol, sexual behavior disorders, eating disorders and for treating migraine.

They may also be used for treating painful muscle contractures in rheumatology and in acute spinal pathology, for treating spastic contractures of medullary or cerebral origin, for the symptomatic treatment of acute and subacute pain of light to moderate intensity, for treating intense and/or chronic pain, neurogenic pain and intractable pain, for treating Parkinson's disease and Parkinson-like symptoms of neurodegenerative origin or induced by neuroleptics, for treating partial primary and secondary generalized epilepsy of simple or complex symptomatology, mixed forms and other epileptic syndromes in addition to another antiepileptic treatment, or in monotherapy, for the treatment of sleep apnea, and for neuroprotection.

A subject of the present invention is also pharmaceutical compositions containing an effective dose of at least one compound according to the invention, in the form of base or of pharmaceutically acceptable salt or solvate, and as a mixture, where appropriate, with one or more suitable excipients.

Said excipients are chosen according to the pharmaceutical form and the desired mode of administration.

The pharmaceutical compositions according to the invention may thus be intended for oral, sublingual, subcutaneous, intramuscular, intravenous, topical, intratracheal, intranasal, transdermal, rectal or intraocular administration.

The unit administration forms may be, for example, tablets, gel capsules, granules, powders, oral or injectable solutions or suspensions, transdermal patches or suppositories. Pomades, lotions and eyedrops may be envisioned for topical administration.

By way of example, a unit form of administration of a compound according to the invention in the form of a tablet may comprise the following components:

| | |
|---|---|
| Compound according to the invention | 50.0 mg |
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

Said unit forms are dosed to allow a daily administration of from 0.01 to 20 mg of active principle per kg of body weight, according to the galenical form.

There may be special cases in which higher or lower doses are appropriate; such doses do not depart from the context of the invention. According to the usual practice, the dosage that is appropriate to each patient is determined by the medical practitioner according to the mode of administration, the weight and the response of said patient.

According to another of its aspects, the present invention also relates to a method for treating the pathologies indicated above, which comprises the administration, to a patient, of an effective dose of a compound according to the invention, or of a pharmaceutically acceptable salt or hydrates or solvates thereof.

What is claimed is:

1. A compound of formula (I)

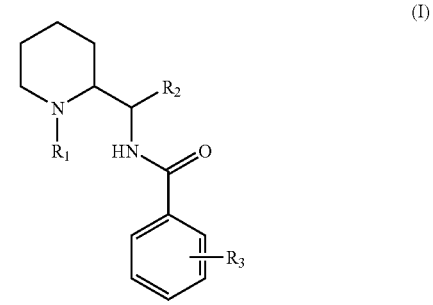

(I)

in which

R$_1$ represents either a hydrogen atom, or a linear or branched (C$_1$-C$_7$)alkyl group optionally substituted with one or more fluorine atoms, or a (C$_3$-C$_7$)cycloalkyl group, or a (C$_3$-C$_7$)cycloalkyl(C$_1$-C$_3$)alkyl group, or a phenyl(C$_1$-C$_3$)alkyl group optionally substituted with one or two methoxy groups, or a (C$_2$-C$_4$) alkenyl group, or a (C$_2$-C$_4$)alkynyl group;

R₂ represents a pyridyl, furyl, thienyl, thiazolyl or oxazolyl group, this group being optionally substituted with one or more substituents chosen from halogen atoms and trifluoromethyl and linear or branched ($C_1$-$C_6$)alkyl and ($C_1$-$C_6$)alkoxy groups;

R₃ represents either a hydrogen atom, or one or more substituents chosen from halogen atoms and trifluoromethyl, linear or branched ($C_1$-$C_6$)alkyl, ($C_3$-$C_7$)cycloalkyl, ($C_1$-$C_6$)alkoxy, phenyl, cyano, acetyl, benzoyl, ($C_1$-$C_6$)thioalkyl, ($C_1$-$C_6$)alkylsulfonyl, carboxyl or ($C_1$-$C_6$)alkoxycarbonyl groups, or a group of general formula $NR_4R_5$ or $SO_2NR_4R_5$ or $CONR_4R_5$ in which $R_4$ and $R_5$ each independently represent a hydrogen atom or a linear or branched ($C_1$-$C_6$)alkyl or ($C_3$-$C_7$)cycloalkyl group, or $R_4$ and $R_5$ form, with the nitrogen atom that bears them, a pyrrolidine, piperidine or morpholine ring;

in the form of free base or of acid-addition salt, hydrate or solvate.

2. A medicament which comprises a compound as claimed in claim 1, or an addition salt of this compound with a pharmaceutically acceptable acid or alterative a hydrate or a solvate of the compound of formula (I).

3. A pharmaceutical composition which comprises a compound as claimed in claim 1, or a pharmaceutically acceptable salt, a hydrate or a solvate of said compound and at least one pharmaceutically acceptable excipient selected according to the pharmaceutical formand the intended mode of administration.

4. A method for treating a behavioral disorder selected from dementia, psychoses, anxiety, panic attacks, phobias, compulsive obsessive disorders, depression, alcohol abuse, sexual behavior disorders, eating disorders and migraine, as well as for neuroprotection, which comprises, administering to a patient with said disorder a therapeutically effective amount of a compound as claimed in claim 1.

5. The method of claim 4 wherein said condition is selected from contracture, pain, Parkinson's disease, epilepsy, and sleep apnea.

* * * * *